United States Patent
Matsumoto et al.

(10) Patent No.: US 7,205,429 B2
(45) Date of Patent: Apr. 17, 2007

(54) METHOD FOR DISPOSAL OF WASTE FROM ACRYLIC ACID PROCESS AND ACRYLIC ESTER PROCESS

(75) Inventors: Yukihiro Matsumoto, Kobe (JP); Takeshi Nishimura, Himeji (JP); Kenji Sanada, Himeji (JP); Harunori Hirao, Himeji (JP)

(73) Assignee: Nippon Shokubai Co., Ltd, Osaka (JP)

( * ) Notice: Subject to any disclaimer, the term of this patent is extended or adjusted under 35 U.S.C. 154(b) by 538 days.

(21) Appl. No.: 10/664,237

(22) Filed: Sep. 17, 2003

(65) Prior Publication Data

US 2004/0055970 A1   Mar. 25, 2004

(30) Foreign Application Priority Data

Sep. 19, 2002 (JP) ............................. 2002-273333

(51) Int. Cl.
*C07C 67/48* (2006.01)
*C07C 57/02* (2006.01)

(52) U.S. Cl. .................................... 560/218; 562/598
(58) Field of Classification Search .................... None
See application file for complete search history.

(56) References Cited

U.S. PATENT DOCUMENTS

| 4,418,045 | A |   | 11/1983 | Sato et al. ................. 423/245 |
|---|---|---|---|---|
| 4,618,709 | A | * | 10/1986 | Sada et al. ................. 562/532 |
| 4,751,005 | A |   | 6/1988  | Mitsui et al. ............... 210/759 |
| 5,734,075 | A | * | 3/1998  | Fauconet et al. ........... 560/218 |
| 6,071,976 | A |   | 6/2000  | Dairoku et al. .............. 521/50 |
| 6,107,358 | A |   | 8/2000  | Harada et al. ............. 521/133 |
| 6,174,978 | B1 |  | 1/2001  | Hatsuda et al. ............ 526/240 |
| 6,241,928 | B1 |  | 6/2001  | Hatsuda et al. ............ 264/216 |
| 6,348,638 | B1 |  | 2/2002  | Schliephake et al. ....... 588/205 |
| 6,414,183 | B1 |  | 7/2002  | Sakamoto et al. .......... 560/218 |

FOREIGN PATENT DOCUMENTS

| JP | A-53-1420057 | 12/1978 |
|---|---|---|
| JP | B-63-067090  | 12/1988 |
| JP | B-07-112555  | 12/1995 |
| JP | A-2000-514419 | 10/2000 |
| JP | A-2001-181233 | 7/2001 |

* cited by examiner

*Primary Examiner*—Paul A. Zucker
(74) *Attorney, Agent, or Firm*—Mathews, Shepherd, McKay & Bruneau, P.A.

(57) ABSTRACT

This invention is providing a method for efficient treatment of the waste material from a process for production of acrylic acid and an acrylic ester. This is a method for the disposal of waste material, which at least one waste material selected from the group consisting of waste oil, waste water, and waste gas emitted from a process for production of acrylic acid is/are purified with at least one waste material selected from the group consisting of waste oil, waste water, and waste gas emitted from a process for production of an acrylic ester jointly. The efficiency of the treatment is enhanced by simultaneously treating the waste material.

9 Claims, 2 Drawing Sheets

METHOD FOR DISPOSAL OF WASTE FROM ACRYLIC ACID PROCESS AND ACRYLIC ESTER PROCESS

BACKGROUND OF THE INVENTION

1. Field of the Invention

This invention relates to a method for the disposal of a waste material from a process for production of acrylic acid and a process for production of acrylic ester, and further from a process for production of polyacrylic acid. More particularly relates to a method for the disposal of the waste material, specifically the waste oil, waste water, and waste gas emitted from the process for production of acrylic acid, the waste oil, waste water, and waste gas emitted from the process for production of an acrylic ester, and further the waste water and waste gas emitted from the process for production of polyacrylic acid (salt), by combustion of the waste material aimed at preventing the piping of a combustion furnace from blocking and the interior of the furnace from generating a blocking material thereby fulfilling environmental conservation of marked advantage.

2. Description of the Related Art

Acrylic acid is a versatile chemical substance and is generally produced on a large scale by the reaction of catalytic gas phase oxidation of propylene, for example. Since this reaction of catalytic gas phase oxidation yields low boiling substance, high boiling substance, etc. as secondary products besides forming acrylic acid, the acrylic acid is purified by removing them in various steps. The impurities which have been separated and removed during the process for obtaining an object from a raw material, therefore, are discharged as waste gas, waste water, waste oil, etc from the process. The waste gas and the waste liquid which are discharged from the process of a commercial scale are proportionately large amounts.

Such waste material as the waste gas and the waste liquid is required to be purified in a high degree and disposed from the viewpoint of preventing the environment from being polluted and the cost for the purification of such waste material is required to be decreased in order to repress the total cost of production. As a technique for accomplishing these requirements, the official gazette of JP-B-63-67,090 discloses an apparatus for the disposal of the waste gas by using a heat exchanger. The official gazette of JP-B-07-112555 discloses a method for the disposal of a waste water containing not only an organic acid but also an ester and an aldehyde thereof by a treatment with an alkali, concentration, and incineration. This method comprises the steps of adding an alkaline substance to the waste water until the resultant pH value reaches a level of not less than 12 thereby inducing a reaction capable of deriving an involatile compound and a volatile compound, removing at least part of the volatile compound by gasification, further concentrating the remaining waste water, and thereafter burning the concentrate. In view of the adverse situation that since the waste water resulting from the neutralization of an acidic substance intermittently emits an organic acid, the resultant condensed water suffers the COD thereof to rise to the extent of rendering a biochemical treatment difficult to effect necessary disposal, the invention of this official gazette contemplates providing a method for the disposal of the waste water by separating a volatile organic acid and an involatile organic acid and adjusting the COD value in a range allowing the disposal to be fulfilled effectively.

The official gazette of International Unexamined Patent Publication No. 2000-514419 discloses a technique which comprises burning a gaseous low boiling component by-produced during the production of (meth)acrylic acid and supplying the other component such that the low boiling or medium boiling component which is dissolved in water and added to the step of burning the gaseous low boiling component. This invention concerns a method for discarding the second component of a low boiling, medium boiling, and high boiling substance formed in the production of (meth) acrylic acid and characterized by burning the gaseous low boiling second component and meanwhile adding the low boiling and medium boiling second component dissolved in water together with the high boiling second component.

The produced acrylic acid is used as a raw material for various chemical products. The acrylic acid obtained from an acrylic acid producing plant is supplied to an acrylic ester producing plant or water absorbing resin such as polyacrylic acid producing plant, which is built at the same place or adjoining the site of the acrylic acid producing plant and put to production therein in a continued process. When an acrylic ester or polyacrylic acid is produced at the same place or adjoining the site for the acrylic acid producing plant, the process for the production of the acrylic ester and the process for the production of the polyacrylic acid also emit such impurities as waste gas, waste water, and waste oil. These plants desire to employ a technique capable of efficiently purifying these impurities in a high degree and disposing them.

As such a technique, the official gazette of JP-A-53-142057 discloses a method for purifying an alkali salt-containing waste water emanated from an acrylic ester production process. In a process for recovering acrylic acid from a gas phase mixture obtained by the reaction of catalytic gas phase oxidation of propylene or acrolein, purifying and esterifying the recovered acrylic acid, subjecting the produced mixture to alkali cleaning, and eventually recovering an acrylic ester, the method of this official gazette comprises exposing the gas phase mixture to the waste water of alkali cleaning heated in advance to a temperature higher than the gas phase mixture thereby causing the water component contained in the waste water to vaporize into the gas phase mixture or subjecting the waste water of alkali cleaning which has decreased the water content to disposal by incineration. This method treats the gas phase mixture and the waste water of alkali cleaning separately.

The method which is disclosed in the official gazette of JP-A-53-142057, however, is directed exclusively toward the gas phase mixture and the waste water of alkali cleaning and is not sufficient to dispose of other waste.

Generally, when the waste oil discharged in a process for the production of acrylic acid is burnt, since acrylic acid has high viscosity, the waste oil disposed of as it is by the combustion tends to clog the piping of the combustion furnace. When the waste oil is used as the fuel for the disposal by incineration, the incineration suffers from such problems as encountering difficulty in ensuring just enough supply of the fuel and entailing possible excess generation of combustion energy. It is further at a disadvantage in inducing the incinerator to form a deposit on the inner wall thereof and consequently causing the incinerator to undergo accelerated deterioration and, when the waste gas arising from the incineration is burnt by itself, causing the heat exchanger used for the burning to yield to corrosion readily and rendering the combustion itself difficult to carry out. The waste gas, similarly to the waste liquid, has the possibility of forming a deposit on the inner wall of the heat exchanger and consequently curtailing the service life of the heat exchanger.

This invention has been initiated with a view to solving the problems and is aimed at providing a method for enabling the waste gas, waste oil, and waste water emitted from the process for production of acrylic acid and the waste gas, waste water, and waste oil emitted from the process for production of acrylic acid, acrylic ester and/or polyacrylic acid (salt) to be purified in high degree and disposed jointly.

SUMMARY OF THE INVENTION

A study conducted on the waste material from the process for production of acrylic acid and the process for production of an acrylic ester to determine their properties and amounts thereof has yielded the knowledge that by simultaneously disposing of the waste material from the process for production of acrylic acid and the process for production of an acrylic ester, it is made possible to decrease the total fuel required for the combustion, impart an increased service life to the apparatus for the disposal and simplify the operation of treatment as well through adjustment of the solid state physical properties of the waste materials and cut the load on the environment.

To be specific, this invention concerns a method for the disposal of waste matter, characterized by subjecting at least one waste material selected from the group consisting of waste oil, waste water, and waste gas emitted from the process for production of acrylic acid and at least one waste material selected from the group consisting of waste oil, waste water, and waste gas emitted from the process for production of an acrylic ester jointly to purification.

The waste oil emitted from the process for production of acrylic acid can be used as the fuel for combustion. When it is used exclusively in the process for production of acrylic acid, however, the fuel is wasted because of shortage of the waste water. When the waste oil is directly introduced into the device for combustion, it has the possibility of clogging the piping of the device or forming a deposit on the inner wall of the device because it has a high degree of viscosity. By diluting the waste oil from the process for production of acrylic acid with the waste water from the process for production of an acrylic ester and subjecting the diluted waste oil and the waste water from the process for production of an acrylic ester jointly to the treatment of combustion with the waste oil from the process for production of a acrylic ester as the fuel, therefore, it is made possible to utilize the fuel for combustion effectively, lower the degree of viscosity of the waste oil and ensure smooth progress of the treatment of combustion, and prevent the device from forming a deposit on the inner wall in consequence of the dilution of the fuel. Particularly since the waste water from the process for production of acrylic acid has a higher COD than the waste water from the process for production of an acrylic ester, the treatment of combustion can be linked with the environmental conservation. When the waste water from the process for production of an acrylic ester is incorporated to form a fuel, the occurrence of a deposit on the inner wall of the device can be effectively repressed because the waste water has included such an alkaline substance as sodium hydroxide as an extraneous substance. The sulfur concentration in the waste gas from the process for production of an acrylic ester can be lowered and the heat exchanger for recovery of heat can be prevented from being corroded by the simultaneous treatment of this waste gas and the waste gas from the process for production of acrylic acid. Further, the practice of subjecting the waste water and/or the waste gas from the process of production of acrylic acid, particularly from the process for production of an absorbing resin jointly to the treatment of combustion is recommended.

Thus, according to this invention, by utilizing the energy generated during the disposal of the waste material and the product of the disposal such as the treated water in the process for production of acrylic acid, it is made possible to unify the disposal of the waste material and the production of the object, decrease the number of steps in the whole process of production, cut the cost of production, contribute to decreasing the site for the disposal, ensure effective utilization of energy and raw materials, and lessen the load on the environment.

According to the present invention, during the disposal of the waste matter from the process for production of acrylic acid and the process for production of an acrylic ester, by burning the waste oil emitted, waste water, and waste gas from the process for production of acrylic acid and the waste oil, waste water, and waste gas from the process for production of an acrylic ester, it is made possible to prevent the piping of the device for combustion from being clogged and the inner wall surface of the device from being covered with a deposit and effect the environmental conservation in an excellent manner. By simultaneously disposing of the waste matter from an adjoining process for production, the disposal can be attained with excellent efficiency.

DESCRIPTION OF THE PREFERRED EMBODIMENTS

The first aspect of this invention is a method for the disposal of waste material, which comprises purifying at least one waste material selected from the group consisting of waste oil, waste water, and waste gas emitted from a process for production of acrylic acid and at least one waste material selected from the group consisting of waste oil, waste water, and waste gas emitted from a process for production of an acrylic ester jointly.

The process for production of acrylic acid contemplated by this invention does not need to be particularly restricted on account of the kind of raw material and the type of steps of production. Generally, the process which produces acrylic acid by subjecting propylene or acrolein to a reaction of catalytic gas phase oxidation, absorbing the product of the reaction with an absorbent thereby obtaining an acrylic acid-containing solution, and separating a low boiling substance and a high boiling substance contained in the solution thereby purifying the solution can be cited as an example. By the same token, the process for production of an acrylic ester does not need to be particularly restricted on account of the kind of raw material or the type of steps of production. Generally, the acrylic ester is the product of esterification of acrylic acid and a fatty acid having a linear or branched chain of a carbon number in the range of 1–12 and it is produced by forming the product of esterification by using an acid catalyst or a basic catalyst and then separating the solvent, a low boiling substance, and a high boiling substance from the product thereby purifying it.

The term "polyacrylic acid (salt)" refers to polymer or co-polymer which has acrylic acid and/or a salt thereof as a main component which contains acrylic acid and/or a salt thereof preferably at a concentration of not less than 70 mol %, and more preferably at a concentration of not less than 90 mol %.

The term "waste gas" as used in this invention refers to a gaseous substance which is discharged from the system for the sake of rejection during the execution of the process for production of acrylic acid, the process for production of acrylic ester, and the process for production of polyacrylic acid (salt). This gas contains combustible compounds such as, for example, hydrocarbons having carbon numbers in the range of 1–6, carbon monoxide, organic acids, aldehydes, esters, and alcohols. The term applies not only to the waste gas which occurs during the production of acrylic acid or an acrylic ester but also to the waste gas which occurs while the device relating to the operation of purification is being cleaned or driven. As concrete examples of the waste gas emitted from the process for production of acrylic acid, the gas discharged as from the heat exchanger and the residual gas discharged from the absorption column may be cited. As concrete examples of the waste gas emitted from the process for production of an acrylic ester, the gas discharged from the reactor for esterification and the gas discharged from the heat exchanger may be cited. As concrete examples of the waste gas emitted from the process for production of polyacrylic acid (salt), the exhaust gas from the polymerizing device, the drying gas used for drying polyacrylic acid (salt), preferably a water absorbing resin, and the exhaust gas from the step for modification such as the surface cross-linkage, following the step for drying may be cited.

The term "waste oil" as used herein refers to an oily substance which is discharged from the system for the sake of rejection during the execution of the process for production of acrylic acid and the process for production of an acrylic ester, namely a liquid which has an organic substance as a main component and is allowed to contain water to the limit of solubility. As concrete examples of the waste oil, the residual liquid of distillation containing a high boiling impurity and the liquid product of distillation containing a low boiling impurity may be cited. This term, similarly to that of "waste gas," applies not only to the waste oil which occurs during the production of acrylic acid or acrylic ester but also to the waste oil which occurs while the device relating to the operation is being cleaned or driven.

The term "wastewater" as used herein refers to an aqueous substance which is discharged from the system during the execution of the process for production of acrylic acid, the process for production of acrylic ester, and the process for production of polyacrylic acid (salt), namely a liquid which has a water as a main component and is allowed to contain an organic substance to the limit of solubility. This term applies not only to the waste water which occurs during the production of acrylic acid, an acrylic ester, and polyacrylic acid (salt) but also to the waste water which occurs while the device relating to the operation is being cleaned or driven. As concrete examples of the waste water, the water formed during the reaction of a raw material for the production of acrylic acid, the waste water generated from the water supplied to the process such as absorbed water, extracting agent, neutralizing agent, and water in the air, the waste water formed by neutralization, the waste water generated for driving such a device as the ejector, and what is obtained by absorbing the waste gas with a solvent such as the aqueous NaOH solution which concentration is not particularly restricted, but preferably in the range of 0.01 wt. % to saturated concentration, and more particularly in the range of 0.1–40 wt. % may be cited. Since this invention is directed toward the waste oil, waste water, and waste gas produced from various processes of treatment, the waste oil, waste water, and waste gas do not need to be particularly restricted on account of the kind of material and/or substance contained therein.

The term "lowboiling substance" as used in this invention refers to a substance having a lower boiling point than the object of production in the standard condition and the term "high boiling substance" refers to a substance having a higher boiling point than the object of production under the standard condition. Incidentally, the term "object of production" refers to acrylic acid in the process for production of acrylic acid, an acrylic ester in the process for production of an acrylic ester, and polyacrylic acid (salt) in the process for production of polyacrylic acid (salt).

The term "distilling column" as used in this invention refers, despite a name of that, to a wide variety of devices used for separating components contained in a given substance by virtue of difference in boiling point such as, for example, a recovering column, an absorption column, a dehydrating column, an azeotropic separation column, a light-ends cut column, a heavy-ends cut column, an acetic acid separating column, a purifying column, and a thin-film evaporator.

The term "purification" embraces distillation, stripping, crystallization, extraction, and absorption. The term "distillation" mentioned above refers to a method which comprises heating a given solution to the boiling point thereof thereby separating volatile components contained therein, the term "stripping" refers to a method which comprises supplying a stripping gas into a given solution thereby inducing transfer of a gas or a vapor dissolved in the solution into a gas phase, and the term "crystallization" means the separation of an object in the form of crystals.

First, the generation of waste gas, waste oil, and waste water in the method of this invention will be explained below with reference to FIG. 1 which illustrates a process for producing acrylic acid from the reaction product of propylene and/or acrolein and a process for producing an acrylic ester by using the acrylic acid produced by the process mentioned above. This statement is not meant to restrict this invention to the following process of production. This process of production may be properly modified within the range in which the effect of this invention is not obstructed. Thus, the waste gas, waste oil, and waste water emitted from the process for production of acrylic acid and the waste gas and waste water emitted from the process for production of an acrylic ester are not meant to be restricted to those of the following kinds. The other waste gas, waste oil, and waste water than those cited above as concrete examples can be properly treated similarly by the method contemplated by this invention.

In the process for production of acrylic acid, a raw material gas 1 containing raw material components, inert gas, molecular oxygen, steam, etc. is supplied to a reactor 10 for the catalytic gas phase oxidation to effect the reaction of the raw material for the catalytic gas phase oxidation with a molecular oxygen-containing gas. To be specific, the raw material gas is supplied to the reactor 10 such as a shell-and-tube type reactor packed with an oxidizing catalyst 11. Acrolein is formed when propylene is oxidized as a raw material component. Acrylic acid is obtained by further subjecting the acrolein to the reaction of catalytic gas phase oxidation. As the raw material, either of propylene and propane (hereinafter occasionally referred to briefly as "propylene, etc.") may be used. The reaction conditions for acrylic acid such as the raw material gas to be used, oxidizing catalyst, inert gas, molecular oxygen-containing gas, and reaction temperature may be selected from among the heretofore known conditions for the process of reaction of acrylic acid.

The raw material gas is composed of one or more raw material components selected from among propylene, propane, and acrolein and used in a concentration in the range of 1–15 vol. %, molecular oxygen used in an amount 1–3 times the amount of the raw material components, and an inert gas such as steam and carbon dioxide used in an amount accounting for the balance. Though the reactor for performing the reaction of catalytic gas phase oxidation does not need to be particularly restricted, the shell-and-tube type reactor may be preferably used in respect of the excellent efficiency of reaction. The acrylic acid is produced by the one-stage reaction when acrolein is used as the raw material component or by the so-called two-stage catalytic gas phase oxidation reaction when propylene is used as a raw material component. The former stage catalyst and the latter stage catalyst to be used for the two-stage reaction of catalytic gas phase oxidation do not need to be particularly restricted. A molybdenum-bismuth type catalyst and a molybdenum-vanadium type catalyst, for example, may be respectively used.

The acrylic acid-containing gas obtained by the reaction of catalytic gas phase oxidation is supplied to an acrylic acid absorption column 20. This column constitutes a step for absorbing the acrylic acid contained in the gas produced by the step of reaction with an aqueous absorbent. The conditions of the absorption such as the gas component composition of the reaction gas, composition of the absorbent, and absorption temperature may be selected from among the heretofore known conditions for the step of absorbing acrylic acid. The gas may be supplied to the absorption column 20 after it has been cooled. This cooling is advantageous because the efficiency of absorption is enhanced in accordance as the gas temperature is lowered.

While the acrylic acid-containing gas is introduced into the absorption column 20, an absorbent 21 capable of absorbing acrylic acid is introduced into the column 20 via the upper part thereof and brought into counter-current contact with the gas and consequently allowed to absorb the acrylic acid.

As the absorbent 21, such a low boiling solvent as water having a lower boiling point than acrylic acid can be used. The residual product in the absorption column 20 after the collection of acrylic acid is discharged as an exhaust gas via the top of the absorption column 20. This exhaust gas is the reaction gas which has escaped the absorption. Thus, part of this exhaust gas may be circulated to the reactor 10 and part thereof may be subjected as a waste gas 23 to a treatment for purification.

When a high boiling solvent having a higher boiling point than acrylic acid is used as an absorbent 21, the acrylic acid-containing gas is supplied to the absorption column 20 and, at the same time, a mixed solvent of diphenyl ether and a biphenyl, for example, is supplied as a high boiling solvent to the absorption column 20 and they are brought into gas-liquid contact therein. Consequently, the acrylic acid is absorbed by causing part of the reaction gas to be absorbed in the high boiling solvent. The reaction gas which remains in the absorption column 20, similarly to the case of use of the aqueous absorbent, is discharged via the top of the absorption column 20. This gas may be circulated to the reactor 10 and part thereof may be subjected as a waste gas to a treatment for purification.

The absorbent 21, for the purpose of preventing itself from polymerizing such a polymerizing substance as acrylic acid, may contain one or more compounds selected from the group consisting of N-oxyl compounds, phenol compounds, manganese salts such as manganese acetate, copper salts of dialkyldithiocarbamic acids such as copper dibutylthiocarbamate, nitroso compounds and amine compounds, and phenothiazine.

In the bottom liquid of the absorption column 20, by-products such as formaldehyde, acrolein, furfural, benzaldehyde, formic acid, acetic acid, maleic acid, and acrylic acid oligomer, and additives such as polymerization inhibitor remain.

When the absorbent for acrylic acid is a low boiling substance such as water, the obtained acrylic acid-containing solution is introduced into an azeotropic dehydrating column 30 and, together with an azeotropic solvent subsequently supplied thereto, left undergoing azeotropic distillation therein. The operating conditions of the azeotropic dehydrating column 30 do not need to be particularly restricted but may be arbitrarily selected from among the conditions which are adoptable at all for the process of producing acrylic acid.

On this occasion, the solution may be supplied to a distilling column 22 and deprived of such a low boiling substance as acrolein and the bottom liquid of the column may be supplied to the azeotropic dehydrating column 30. The low boiling substance which has been removed in the distilling column 22 may be advanced to the absorption column 20 and treated as the exhaust gas from the absorption column 20. Meanwhile, the exhaust gas from the distilling column 22 may be treated as separated from the exhaust gas from the absorption column 20. When this exhaust gas happens to be a waste gas destined to be expelled from the system, it may be treated for purification by the method of this invention. Incidentally, the exhaust gas from the distilling column 22 may be supplied to other arbitrarily selected step and used therein.

This invention will be described below by citing an example of performing the azeotropic dehydrating distillation by the use of an azeotropic solvent. An arbitrary method of distillation may be adopted in the place of the method of azeotropic distillation to effect separation and removal of an impurity from the acrylic acid solution. In this case, the combination of distilling conditions, number of operations of distillation, and apparatus for distillation may be properly selected to suit the purpose of the distillation.

As the azeotropic solvent, any of the well-known azeotropic solvents may be used. It is particularly preferable to use an azeotropic solvent which by nature is incapable of forming an azeotrope with acrylic acid. The azeotropic solvent which is sparingly soluble in water proves advantageous because it can be easily separated from the distillate water phase when the azeotropic solvent is recovered and put to reuse. As concrete examples of the azeotropic solvent which answers this description, toluene, xylene, hexane, heptane, cyclohexane, methylisobutyl ketone, and butyl acetate may be cited. These azeotropic solvents may be used either singly or in the form of a mixture of two or more members. It is preferable to use such an azeotropic solvent in an amount enough to produce a fully satisfactory effect of separation from the viewpoint of enhancing the efficiency of azeotropic distillation.

By the azeotropic dehydration mentioned above, the by-products having lower boiling points than acrylic acid and such low boiling substances as water are discharged as the distillate together with the azeotropic solvent through the top of the column. Generally, the azeotropic dehydrating column has an oil-aqueous separator attached as an accessory therefore to the top the column and the azeotropic solvent contained in an oil phase 31 is refluxed to the azeotropic dehydrating column 30. This invention allows part of the oil phase 31 to be discharged from the system and treated for purification. The aqueous phase which can be used as the absorbent 21 in the absorption column 20 may be optionally treated as a waste water. The reason for this optional treatment is that the continuous use of the water phase has the possibility of heightening the concentration of the low boiling substance in the water phase and degrading the efficiency of purification. Optionally, a step of treatment for recovering the azeotropic solvent component remaining dissolved in a water phase 32 may be incorporated in the operation and utilized for disposing the residue as waste water.

Further, such high boiling substances as maleic acid and acrylic acid dimer and acrylic acid, and the polymerization inhibitor are withdrawn through the bottom of the column and supplied to the subsequent step.

The treatment for azeotropic dehydration removes the water contained in the acrylic acid-containing aqueous solution. This step of azeotropic dehydration may be followed by a step for the removal of a low boiling substance. Generally, the step for separation of a high boiling substance and the other step for purification are carried out after the dehydrating treatment. The method for purification of acrylic acid may be any of the combinations of the heretofore known methods for purification. Thus, the azeotropic dehydration may be followed first by the removal of the low boiling substance such as, for example, acetic acid and then by the removal of the high boiling substance. The purification of acrylic acid does not need to be restricted to the method of distillation described above but may be attained by crystallization instead.

Figure 1:
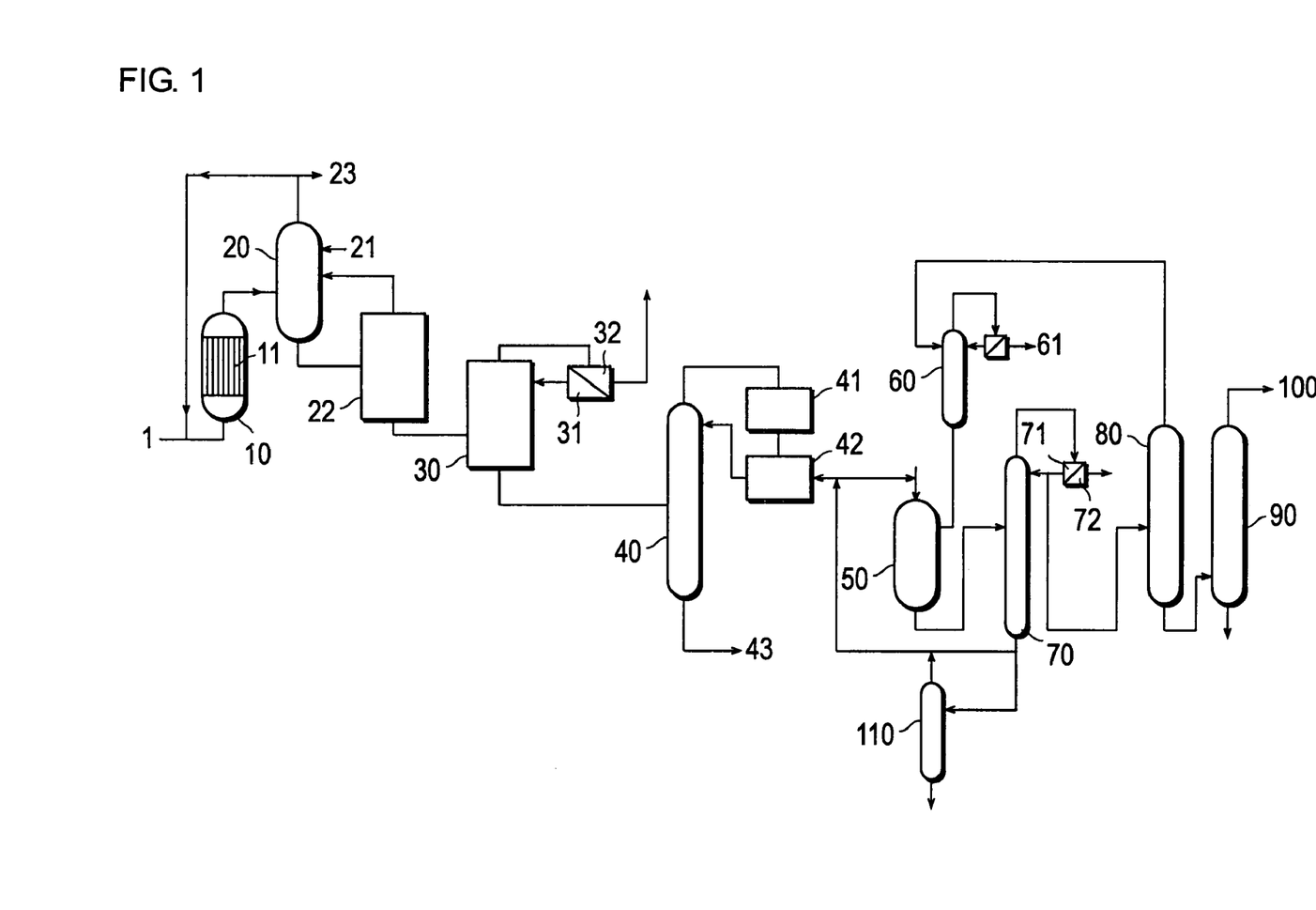
FIG. 1 is a flow diagram illustrating the outline of a process for production of acrylic acid inclusive of a process for production of an acrylic ester.

When a high boiling solvent is used as the absorbent, the acrylic acid-containing solution is supplied to a light-ends cut column, though not illustrated in FIG. 1, to remove such low boiling substances as formic acid, acetic acid, acrolein, formaldehyde, acetaldehyde, and water which are contained in the acrylic acid-containing solution. The separating conditions for the light-ends cut column may be selected from those used by the heretofore well-known methods. Since the distillate emanating from the light-ends cut column still contains a considerable amount of acrylic acid, it may be circulated to the absorption column 20 so as to enhance the percentage of recovery of acrylic acid. In any event, the gas and liquid which are discharged from the light-ends cut column may be treated as waste gas, waste oil, and waste water for purification in this invention.

Then, the bottom liquid of the azeotropic dehydrating column is introduced into a heavy-ends cut column 40. For the purpose of decreasing the amount of an impurity contained in the bottom liquid of the column, still another step for distillation may be incorporated prior to the introduction of the bottom liquid into the heavy-ends cut column 40. For example, the bottom liquid of the column may be introduced into an arbitrary step such as an acetic acid separating column or a heavy-ends cut column which is not illustrated in the diagram with a view to decreasing the impurity. In this invention, the exhaust oil discharged from the system can be disposed of as waste oil by the incorporated step described above. The solution may be introduced into the azeotropic dehydration column 30 and subjected to one cycle of the operation of distillation to produce acrylic acid containing substantially no acetic acid, water, or azeotropic solvent and this acrylic acid may be supplied to a step for separation and purification, for example. This invention allows the steps for separation and purification of acrylic acid which can be adopted for the common process for production of acrylic acid to be arbitrarily combined properly to suit the purpose and the conditions of the step. The gas, water, and oil which are discharged from the process in this case can be treated for purification.

In the heavy-ends cut column 40 illustrated in the diagram, a distilling operation is performed with the object of treating the bottom liquid of the azeotropic dehydrating column 30 thereby purifying the acrylic acid in the bottom liquid. By this distillation, acrylic acid containing no high boiling substance is obtained. The acrylic acid contained in the liquid supplied to the heavy-ends cut column 40 is vaporized by an operation of distillation, and condensed by the operation of a condenser 41 furnished to the top of the column. The resultant condensed liquid is stored in a tank 42 or introduced via the tank 42 into an esterifying reactor 50.

Meanwhile, the high boiling impurity and the polymerization inhibitor which have been contained in the feed liquid are separated from acrylic acid by the distillation mentioned above and accumulated in the bottom of the column to give rise to the bottom liquid of the heavy-ends cut column 40. When the bottom liquid is discharged from the system, it may be treated as waste oil 43 according to the method of this invention.

Incidentally, the polymerization inhibitor may be added for the purpose of precluding polymerization in the azeotropic dehydrating column 30 and the heavy-ends cut column 40 as well. This addition may be effected by mixing the polymerization inhibitor with the feed liquid and introducing the loaded feed liquid into the relevant column through other site. For example, the polymerization inhibitor may be added to the acrylic acid solution destined to be introduced into the column or to the liquid such as the reflux liquid to be introduced into the column and the loaded liquid may be supplied into the column. It is also permissible to supply the polymerization inhibitor directly into the column. To be specific, the polymerization inhibitor may be directly supplied to the column via the bottom thereof by means of air bubbling, for example. Otherwise, the polymerization inhibitor may be indirectly supplied to the column by having this polymerization inhibitor dissolved in other solvent and then causing the resultant solution to be introduced into the column. The greater part of the polymerization inhibitor thus added to the column is recovered in the bottom liquid of the heavy-ends cut column 40 and eventually discharged out of the system.

The method for producing an acrylic ester from acrylic acid does not need to be particularly restricted. One mode of embodying the method for producing the ester by the use of an acid catalyst will be shown below.

The acrylic acid obtained in the heavy-ends cut column 40 is supplied to an esterifying reactor 50 packed with a strongly acidic cation resin as a catalyst and the reactor 50 is then charged with alcohol and other component to form the product of esterification. A distilling column 60 is disposed above the reactor 50 for the purpose of enabling the water formed by the reaction to be removed. This distilling column 60 is capable of disposing the formed water 61 emanating from the distilling column 60 as a waste water. Then, the reaction solution is introduced into an acid separating column 70 so as to expel such low boiling substances as an acrylic ester, unaltered alcohol, and water by distillation via the top of the column. Subsequently, the distillate emanating from the top of the acid separating column 70 is introduced into an oil-aqueous separating device and separated therein into an oil phase 71 containing an acrylic ester and a water phase 72. The oil phase 71 containing the acrylic ester is dehydrated and deprived of a low boiling substance as well in a light-ends cut column 80. Meanwhile, the water phase 71 is discharged from the system and disposed of as a waste water. Incidentally, part of the oil phase 71 may be refluxed to the acid separating column 70.

Meanwhile, the light-ends cut column 80 withdraws the acrylic ester from the bottom liquid thereof and supplies it to a purifying column 90 and expels a finished acrylic ester 100 via the top thereof. The water, alcohol, and other low boiling substance which have been expelled by distillation via the top of the light-ends cut column 80 may be circulated via the distilling column 60 disposed above the esterifying reactor 50 to the esterifying reactor 50.

In the process for producing the acrylic ester as described above, the bottom liquid of the acid separating column 70 contains an acrylic acid dimer together with such raw material components as acrylic acid. Thus, the bottom liquid of the acid separating column 70 may be circulated to the esterifying reactor 50 as illustrated in FIG. 1 or it may be supplied to a heavy-ends cut column 110 disposed independently and allowed therein to induce separation of the acrylic acid oligomer contained therein. Optionally, a dimer decomposing tank may be disposed, though not illustrated in the diagram, and utilized for decomposing the acrylic acid dimer contained in the bottom liquid into acrylic acid. The acrylic acid thus formed may be used again in the process for production of acrylic acid and the process for production of an acrylic ester.

When an acrylic ester is produced, the crude ester may be first washed with an aqueous alkali solution and then washed with water for the removal of the alkali, with the result that the water of alkali cleaning will be discharged. In this invention, the water of alkali cleaning as waste water may be treated for purification.

Incidentally, the method for producing an acrylic ester consists in subjecting acrylic acid and an alcohol to the reaction of dehydration thereby obtaining an ester. As concrete examples of the alcohol which is preferably used for the reaction, various alcohols such as methanol, ethanol, n-butanol, isobutanol, sec-butanol, t-butanol, 1-pentanol, 2-pentanol, 3-pentanol, cyclopentanol, 1-hexanol, 2-hetanol, 3-hexanol, cyclohexanol, 1-heptanol, 2-heptanol, 3-heptanol, 1-octanol, isooctanol, 2-ethylhexanol, isononyl alcohol, and lauryl alcohol may be cited may be cited. These alcohols may be in a linear form or a branched form. They may be used not only singly but also in the form of a mixture of two or more members. Incidentally, the reaction conditions, distillation conditions, and the like for each of the steps described above may be selected from among the heretofore well-known conditions.

In the case of producing polyacrylic acid (salt), though the acrylic acid in the tank 42 can be used in the unmodified form as the raw material, it may be preferably purified, distilled or crystallized further and used in a form containing substantially no aldehyde.

As concrete examples of the polyacrylic acid (salt) contemplated by this invention, water-soluble polyacrylic acid (salt) and water-absorbing resin, water-absorbing polyacrylic acid (salt), may be cited. The polyacrylic acid salts are preferably monovalent salts and more preferably alkalimetal salts and ammonium salts. These polyacrylic acid (salts) may be copolymerized with other monomer, cross-linked with 0.001–5 mol % of a cross-linking agent, or graft polymerized with other hydrophilic polymer such as starch or polyvinyl alcohol. The term "water-soluble polyacrylic acid (salt)" means a polymer which is dissolved substantially at a ratio of 100% in water and the term "water-absorbing resin" means a water-swelling and water-insoluble polyacrylic acid (salt) which has a cross-linked structure and is capable of absorbing not less than 3 times, preferably 10–1,000 times, its own weight of pure water or physiological salt solution and consequently forming a substantially water-insoluble hydrogel which contain not more than 25 wt. %, preferably not more than 10 wt. %, of a water-soluble component. For information on the concrete examples of the water-absorbing resin and the methods for determining solid state physical properties thereof, reference to the official gazettes of U.S. Pat. No. 6,071,976, U.S. Pat. No. 6,107,358, U.S. Pat. No. 6,174,978, and U.S. Pat. No. 6,241,928 are recommended.

As one example of the process for production of polyacrylic acid (salt), a water-absorbing resin is produced by introducing the acrylic acid into a step for neutralization, a step for polymerization of acrylic acid(salt), and a step for drying the obtained polyacrylic acid (salt) and subjecting it to relevant necessary treatments therein. Naturally, other necessary treatments may be performed for the purpose of improving various solid phase physical properties. For example, a cross-linking step may be incorporated during or after the course of polymerization.

The neutralizing step is an arbitrary treatment. A method of mixing a necessary amount of a basic substance in the form of powder or aqueous solution with acrylic acid or with the produced polyacrylic acid (salt) may be cited as a concrete example of this neutralizing step. The method for effecting this step does not need to be particularly restricted but may be selected from among the heretofore well-known methods. Incidentally, the neutralizing step may be performed either before or after the polymerization or both before and after the polymerization.

The basic substance to be used for the neutralization of acrylic acid may be properly selected from among the heretofore well-known basic substances such as, for example, carbonate, hydrogencarbonate, hydrides of alkali metals, ammonia, and organic amines. The degree of neutralization of the polyacric acid does not need to be particularly restricted but may be properly adjusted to a necessary level such as an arbitrary value in the range of 30–100 mol %.

The method for polymerization at the step for polymerization does not need to be particularly restricted but may be properly selected from among the heretofore well-known methods such as polymerization with a radical polymerization initiator, radiation-induced polymerization, electron beam-induced polymerization, and ultraviolet light polymerization with a photosensitizer. The various conditions such as the kind of polymerization initiator and the conditions for polymerization may be arbitrarily selected. Naturally, well-known additives such as a cross-linking agent, other similar monomer, and water-soluble chain transfer agent, and hydrophilic macromolecular compound may be incorporated as occasion demands.

The polyacrylic acid (salt) (hereinafter referred to collectively as "water-absorbing resin") which results from the polymerization may be subjected to a step for drying. The method for effecting this drying does not need to be particularly restricted. The drying may be attained by using any of the heretofore well-known drying means such as, for example, hot air dryer, fluidized-bed dryer, and Nauter type dryer at a necessary drying temperature preferably a level in the range of 70–230° C. The high-temperature gas which has been supplied to the step for drying and emitted therefrom may be discharged in an unmodified form as a waste gas and subjected to the step for the disposal of waste gas contemplated by this invention. Alternatively, it may be introduced into a absorption column and exposed therein to an arbitrary collecting solution such as, for example, an aqueous NaOH solution which is separately introduced into the absorption column, with the result that the waste gas is collected and discharged in the form of waste water and then supplied to the step for the disposal of waste liquid contemplated by this invention. In this invention, it is preferred to be utilized as a drying gas.

As the waste water, waste oil, and waste gas which can be treated for purification in this invention, the washings of the devices used in the process for production of acrylic acid, the process for production of acrylic ester, or the process for production of polyacrylic acid (salt) may be subjected as waste water and waste oil to the treatment for purification. Acrylic acid is a polymerizing compound and, therefore, possibly forms a polymer during the course of production. Thus, there are times when the devices used for the production may be washed with an alkaline cleaning water or with an organic solvent and subsequently washed with water. The waste liquid which occurs in this case may be subjected as waste water or waste oil to a treatment for purification.

Now, the method for treating for purification the waste gas and waste liquid such as a waste water and a waste oil emitted from the process for producing acrylic acid and the waste gas and waste liquid emitted from the process for production of an acrylic ester will be described below. Incidentally, the term "treatment for purification" as used in this specification refers to a method for disposing of a waste material. This term embraces a method which consists in rendering the component contained in the waste gas harmless and releasing the treated waste gas into the ambient air, a method which consists in burning a component contained in the waste water or waste oil thereby converting the organic component into carbon dioxide and water and then releasing the product of conversion into the ambient air, and a method which consists in performing a treatment with activated sludge, a treatment of wet oxidation, or other similar treatment.

The method contemplated by this invention is characterized by causing at least one waste material selected from the group consisting of waste oil, waste water, and waste gas emitted from the process for production of acrylic acid and at least one waste material selected from the group consisting of waste oil, waste water, and waste gas emitted from the process for production of an acrylic ester to be jointly subjected to purification. The waste gas, waste oil, and waste water emitted from the process for production of acrylic acid and the waste gas, waste oil, and waste water emitted from the process for producing an acrylic ester are different in the kind of component contained and in viscosity, amount of emission, concentration, and other characteristic properties. Generally, the waste materials emitted from the process for production of acrylic acid have large amount, high concentration, and high viscosity as compared with the waste materials emitted from the process for production of an acrylic ester. When the waste materials emitted from the process for production of acrylic acid and the waste materials emitted from the process for production of an acrylic ester are separately treated, this separate treatment entails such disadvantages as necessitating a combustion auxiliary for the treatment of the waste materials from the process for production of an acrylic ester and yielding an excess of the waste oil which is usable as the fuel for combustion in the treatment of the waste materials from the process for production of acrylic acid. Thus, this invention has elected to treat jointly the waste materials from the adjoining processes of production. According to this invention, when the waste oil is used as the fuel for the treatment of the waste materials, it gives rise to an excess in the sole treatment of the waste materials from the process for production of acrylic acid and this excess of the waste oil necessitates a separate treatment. When the waste water, waste oil, and waste gas emitted from an adjacent related process for production are simultaneously treated, however, it is made possible to supply the fuel neither too much nor to little, adjust the viscosity of the waste materials as well, and avoid the difficulty of the treatment of purification due to the decline of flowability. In this invention, the waste gas, waste water, and waste oil emitted from the process for production of acrylic acid and from the process for production of an acrylic ester can be supplied in their whole amounts to the treatment for combustion. Their amounts of supply may be properly adjusted to suit the capacity for the treatment of combustion and the residues thereof may be supplied to some other treatment for purification. For the purpose of decreasing the amounts to be treated, the waste oil, waste water, and waste gas may be beforehand concentrated and supplied in the concentrated form to the treatment for purification.

This invention particularly prefers to perform the treatment by combustion on the mixed liquid which comprises at least one of the waste oils emitted from the process for production of acrylic acid and/or the process for production of an acrylic ester and at least one of the waste waters emitted from the process for production of acrylic acid and/or the process for production of an acrylic ester. The combustion of the mixed liquid is at an advantage in enabling the waste oil as the fuel for the treatment of the waste material and enabling the organic substance to be converted by the treatment of combustion into carbon dioxide, water, etc. The waste oil emitted from the process for production of acrylic acid, however, is in too large an amount to be used as the fuel for the treatment by combustion. Further, the waste oil from the process for production of acrylic acid contains maleic acid in a large amount as described above and tends to form a polymer and a deposit. During the course of the production, the temperature is controlled in a range of 50–150° C. for the purpose of precluding the formation of such extraneous substances. At this temperature, the waste oil exhibits an increase in viscosity. When the waste oil with an increased viscosity is transferred to the incinerator and burnt therein as a fuel, the flowability of the liquid being treated in the piping of the incinerator is lowered. In this case, the addition of waste water may be resorted to as a means for preventing the flowability from falling. By subjecting the waste water to the treatment of combustion, it is made possible to use up the excess of the waste oil as the fuel for the combustion. After the dilution with the waste water, the temperature is preferred to be controlled in the range of 20–100° C., preferably in the range of 30–80° C. because the maleic acid in the diluted waste oil tends to form fumaric acid. When the waste water from the process for production of acrylic acid is used as the diluting water for the waste oil, since this waste water has a higher COD level than the waste water from the process for production of an acrylic ester, the treatment of incineration of the diluted waste oil is at an advantage in enabling the purification to proceed more easily and conveniently than the treatment with activated sludge. When the alkali waste water emitted from the process for production of an acrylic ester is additionally incorporated, the occurrence of a deposit in the device of combustion can be precluded and the number of cycles of cleaning given to the device of combustion can be markedly decreased. Since the waste oil from the process for production of an acrylic ester serves as the fuel for combustion, it is preferred to be subjected to the treatment of combustion together with the waste oil from the process for production of acrylic acid.

It is further preferable to have part of the waste water mentioned above subjected to the treatment of combustion and the remainder thereof subjected to the treatment of wet oxidation and/or the treatment with activated sludge. When the waste oil is used as the fuel for combustion, for example, only the portion of the waste water which has a heat balance with the amount of the waste oil is subjected to the treatment for combustion and the remainder thereof subjected to the purification by the treatment of wet oxidation or the treatment with activated sludge. Particularly when the waste oil emitted from the process for production of acrylic acid (hereinafter referred to as "acrylic acid waste oil") and the waste water emitted from the process for production of an acrylic ester (hereinafter referred to as "ester waste water") are jointly subjected to the treatment of combustion, it is made possible to obviate the necessity of using a combustion auxiliary which has been otherwise found indispensable and lower the cost of combustion because the ester waste water has feeble combustibility.

Figure 2:
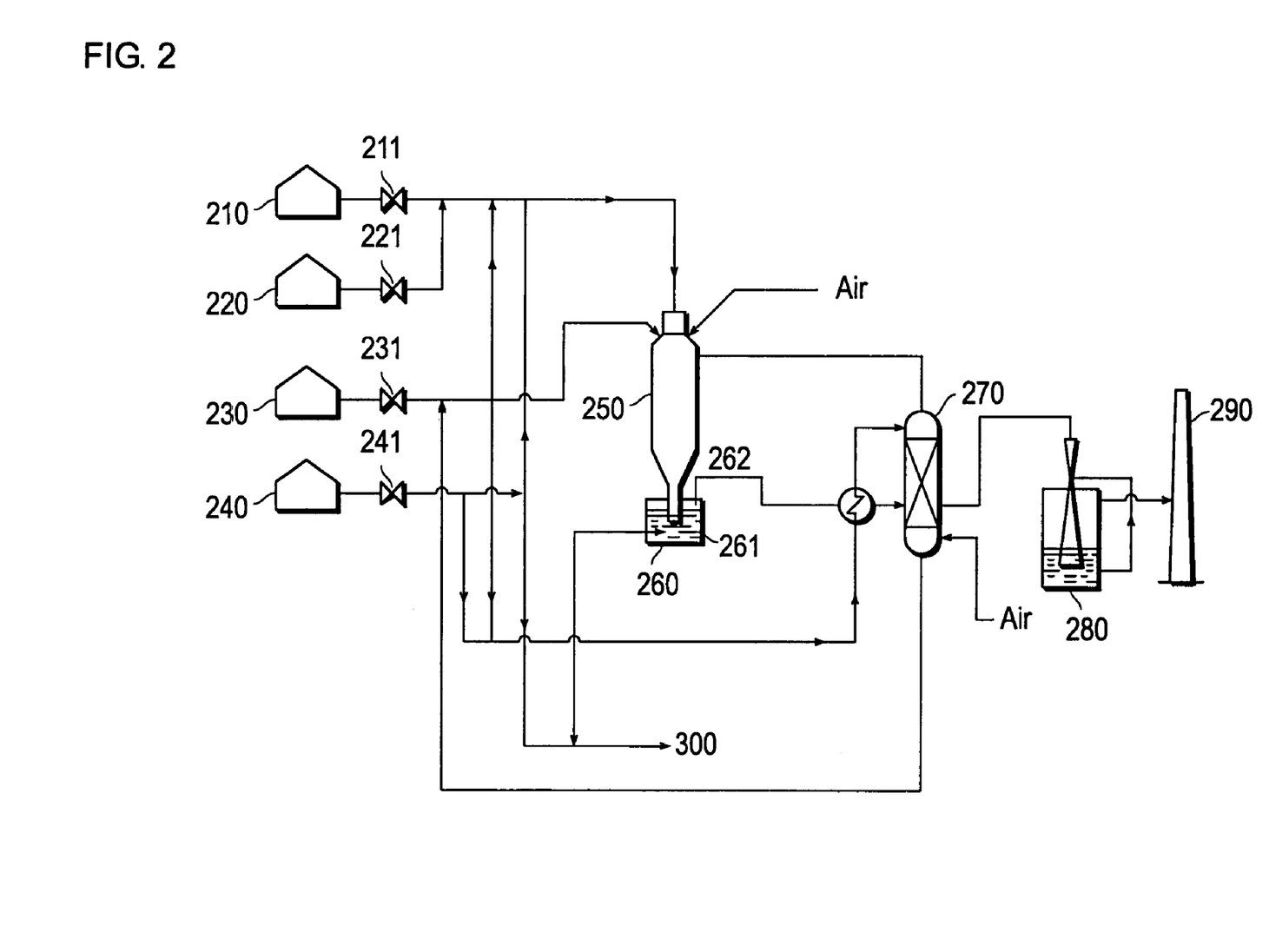
FIG. 2 is a flow diagram illustrating one example of the preferred embodiment of the treatment of combustion in the method for the disposal of the waste matter contemplated by this invention.

One example of the mode of embodying the method for combustion of waste oil and waste water in the method for the treatment of the waste material contemplated by this invention will be explained below with reference to FIG. 2.

The device to be used for the treatment of combustion contemplated by this invention does not need to be particularly restricted. It is recommended to use a heretofore well-known combustion device such as the vertical combustion device or the horizontal combustion device. In the case of the gas combustion, the combustion by the use of a catalyst is recommended.

A waste oil from the process for production of acrylic acid 210 (hereinafter referred to occasionally as "acrylic acid waste oil"), a waste oil from the process for production of an acrylic ester 220 (hereinafter referred to occasionally as "ester waste oil"), a waste water from the process for production of acrylic acid 230 (hereinafter referred to occasionally as "acrylic acid waste water"), and a waste water from the process for production of acrylic ester 240 (hereinafter referred to occasionally as "ester waste water") adjusted to respectively proper amounts with valves 211, 221, 231, and 241 were supplied to a combustion device 250, wherein the waste oils and the waste waters in the incinerator were treated for combustion with the waste oils used as the fuel.

Though the kinds of waste oil and waste water to be supplied to the combustion device 250 do not need to be particularly restricted, they are at least the waste oil from the process for production of acrylic acid and/or the process for production of an acrylic ester and the waste water from the process for production of acrylic acid and/or the process for production of an acrylic ester. More specifically, it is preferable to have the acrylic acid waste oil 210 and the acrylic acid waste water 230 jointly purified. This is because the viscosity of the acrylic acid waste oil 210 can be lowered and the clogging of the piping can be precluded. Further, since the acrylic acid waste water 230 has a higher COD level than the ester waste water 240, the treatment of the combustion of the acrylic acid waste water 230 results in facilitating the treatment of the waste water.

In this invention, it is preferable to apply the whole amount of the acrylic acid waste oil 210 and the whole amount of the ester waste oil 220 and the amount of the acrylic waste water 230 or the ester waste water 240 which is optimum for the purpose of lowering the viscosity of the acrylic acid waste oil 210 to the treatment of combustion. The mixing ratio of the acrylic acid waste oil 210 to the acrylic acid waste water 230 or the ester waste water 240 does not need to be particularly restricted. For the purpose of burning the acrylic acid waste water 230 with high efficiency and lowering the viscosity of the acrylic acid waste oil 210 as well, it is preferable to add the acrylic acid waste water 230 or the acrylic ester waste water in an amount in the range of 3–30 vol. % based on the volume of the acrylic acid waste oil 210 (amount of waste water/amount of waste oil).

The acrylic acid waste oil 210 is preferred to be diluted with the acrylic acid waste water 230 or the ester waste water 240 in the piping before it is supplied to a waste oil tank (not shown). This is because the pipe laid between the process for acrylic acid and the waste oil tank for combustion is generally long and the dilution serves the purpose of preventing the pipe from the trouble of clogging.

The acrylic acid waste oil 210 and the acrylic acid waste water 230 can be introduced via separate feed pipes into the combustion device 250 and burnt therein as kept mixed with each other meanwhile. It is, however, preferable to have the acrylic acid waste oil 210 beforehand mixed with a necessary amount of the acrylic acid waste water 230, introduce the resultant mixed liquid into the combustion device, and introduce the remainder of the acrylic acid waste water 230 separately. This is because the procedure just mentioned is capable of preventing the interior of the feed pipe from being clogged by the adhesion of the acrylic acid waste oil 210 and preventing as well the leading terminal part of the means (such as, for example, a nozzle) for feeding the mixed liquid to the combustion device 250 from being clogged. Further, the use of the mixed liquid mentioned above results in diluting the acrylic acid waste oil 210 having a comparatively high degree of viscosity, which means lowering the viscosity, repressing the clogging of the nozzle even when the liquid is sprayed into the combustion device via such a feed means as the nozzle, and atomizing the mixed liquid to a degree suitable for combustion.

In this invention, for the purpose of lowering the viscosity of the acrylic acid waste oil and for other purposes as well, the ester acid waste water 240 may be burned together with the acrylic acid waste oil 210, the ester waste oil 220, and the acrylic acid waste water 230. In this case, the ester waste water 240, similarly to the acrylic acid waste water 230, may be supplied to the combustion device 250 via a feed pipe different from the feed pipe used for the acrylic acid waste oil 210, for example. The acrylic acid waste oil 210 may be mixed beforehand with the ester waste water 240 and supplied in the mixed state to the combustion device 250. It is also permissible to have the mixed liquid of the acrylic acid waste oil 210 and the acrylic acid waste water 230 with the ester waste water 240 and feed the resultant mixture to the combustion device 250. Incidentally, when the ester waste water 240 and the acrylic acid waste water 230 are together mixed with the acrylic acid waste oil 210, the total amount of the acrylic acid waste water 230 and the ester waste water 240 is preferred to fall in the range of 3–30 vol. % based on the volume of the acrylic acid waste oil 210 as described above. In this case, the mixing ratio of the acrylic acid waste water 230 and the ester waste water 240 does not need to be particularly restricted. When the ester waste oil 220 has a high degree of viscosity and, when used without any modification, threatens to clog the piping of the device give rise to a deposit on the inner wall of the combustion device, it may be diluted beforehand to a proper degree of viscosity with the acrylic acid waste water 230 and the ester waste water 240 similarly to the acrylic acid waste oil 210 and then introduced into the combustion device.

In this invention, during the treatment of the waste oil and the waste water by combustion, the waste gas from the process for production of acrylic acid and the process for production of an acrylic ester (hereinafter referred to occasionally as "acrylic acid waste gas and ester waste gas") (not shown) may be supplied to the combustion device 250 and subjected simultaneously to the treatment for combustion. Incidentally, the acrylic acid waste gas and/or the ester waste gas may be subjected to the treatment of combustion in conjunction with the acrylic acid waste oil 210, the ester waste oil 220, the acrylic acid waste water 230, and the ester waste water 240. The acrylic acid waste gas and the ester waste gas contain organic substances. By the treatment of combustion, such impurities as the organic substances which are contained in these waste gases can be removed. In this case, it is advantageous to have the mixed gas of the two waste gases treated by combustion in conjunction with the acrylic acid waste oil 210 as compared with the combustion of either of the acrylic acid waste gas and the ester waste gas with the acrylic acid waste oil 210. This is because the combustible compound in the ester waste gas is diluted with the acrylic acid waste gas and, as a result, the combustion for removal of the combustible compound in the combustion gas can be carried out with high efficiency. Further, the mixture can be decreased the concentration of the organic substance contained in the ester waste gas and preclude the possibility of clogging the device and the use of the ester waste gas as the diluting gas may be utilized for promoting the cut of the cost.

In this invention, the treatment of the waste gas, waste water, and waste oil by combustion does not need to be restricted to the case of using the waste oil as the fuel for the combustion. It is permissible, for example, to combine arbitrarily the acrylic acid waste water and/or the acrylic acid waste gas with the ester waste water and/or the ester waste gas and subject the resultant combination to the treatment for combustion. By treating the acrylic acid waste gas and the ester waste water together by combustion in conjunction with the ester waste water, for example, it is made possible to have the ester waste water burnt in consequence of the combustion of the waste gas and lower the cost of the fuel. Otherwise, it is permissible to have the ester waste water treated by combustion together with the acrylic acid waste gas or the ester waste gas treated by combustion together with the acrylic acid waste water.

Similarly, by adding the acrylic acid waste water and the ester waste water together and burning them simultaneously, it is made possible to further lower the concentration of the organic substance contained in the acrylic acid waste water. For the purpose of heightening the efficiency of combustion as occasion demands, a combustion auxiliary such as kerosine and air are supplied to the combustion device and burnt therein to have the temperature in the device retained at a temperature in the approximate range of 600–1,200° C. and then the acrylic acid waste water and/or the ester waste water may be supplied by spraying into the device and the acrylic acid waste gas and/or the ester waste gas may be burned therein together.

The temperature of the combustion and the duration of the combustion may be properly selected to suit the performance of the combustion device used, the kind of the waste oil introduced, and the amount of the waste water used.

The method for performing the treatment subsequent to the combustion does not need to be particularly restricted. Generally, the combustion gas 251 emitted from the combustion device 250 is received in a water tank 260 after the solid component contained therein has been removed. The liquid property of a treating water in the water tank may be adjusted to suit the liquid property of the combustion gas and the kind of substance contained therein. When the combustion gas 251 contains a sulfur component and this gas assumes acidity, for example, the acid component is collected in the treating water 261 by alkalinizing the liquid property with sodium hydroxide. This invention uses a polymerization inhibitor. Since the polymerization inhibitor is destined to be contained in the waste oil, the combustion gas 251 possibly entrains a metal originating in the polymerization inhibitor. When this metal is enabled by forming a hydroxide to be precipitated in the water tank 260, the subsequent purification is facilitated by adjusting the liquid property of the treating water 261 in the water tank to alkalinity.

When the treating water 161 in the water tank, after the recovery of an economic metal contained therein, no longer contains any harmful metal or other compound and proves fit to be released safely into a nearby body of water, it is subjected to a treatment for disposal in a nearby body of water. The method for the treatment of the waste material contemplated by this invention is characterized by having the waste oil, waste water, and waste gas from different process for production treated jointly. The method specifically used for the treatment may be selected from among the heretofore well-known methods.

A high-temperature waste gas 262 which has been cleaned with the treating water 261 in the water tank 260 hovers above the water tank. This invention enables the efficiency of treatment to be enhanced by effectively utilizing the thermal energy of the waste gas 262. The acrylic acid waste water 230 and the ester waste water 240 are wholly or partly supplied to a stripping column 270 and heated therein to an elevated temperature with the waste gas and stripped with air. The fuel for the combustion can be decreased by beforehand heating the waste water and then supplying the hot waste water to the combustion device 250. For the purpose of removing the dust entrained by the waste gas 262, the waste gas 262 is released into the ambient air after it has been passed through a venturi 280.

Further, the waste water and/or the waste gas from the process for production of polyacrylic acid (salt) may be supplied to the combustion device of the process for production of acrylic acid and the process for producing an acrylic ester mentioned above. Since the waste water from the process for production of polyacrylic acid (salt) has feeble combustibility, the combustion of this waste water used to require separately a fuel for combustion and boost the cost of combustion. By burning this waste water together with the acrylic acid waste oil and/or the ester waste oil, it is made possible to burn the waste water from the process for production of polyacrylic acid (salt) efficiently with the waste oil of high combustibility. Further, by burning the waste water mentioned above together with the acrylic acid waste oil, it is made possible to lower the concentration of the acrylic acid waste oil and, owing to the inclusion of Na therein, prevent the residue of the acrylic acid waste oil after the combustion from adhering to the inner wall of the combustion device and bring about a marked decrease in the number of cycles of washing given to the combustion device.

This invention particularly prefers the waste gas from the process for production of polyacrylic acid (salt) to be treated by combustion together with the acrylic acid and/or ester waste gas. Since the organic substance contained in the acrylic acid and/or ester waste gas has a high concentration, the simultaneous combustion is capable of lowering the concentration mentioned above and further decreasing the amount of a deposit on the combustion device and the heat exchanger.

In the method of this invention for treating the waste material, though the waste gas can be treated for combustion together with the waste oil or the waste water as described above, it may be treated for combustion by itself. When the acrylic acid waste gas or the ester waste gas used alone exhibits unduly low combustibility in this case, a combustion auxiliary such as kerosine may be supplied to the waste gas for the sake of enhancing the efficiency of combustion. In the treatment of the waste gas by combustion, a catalytic combustion device may be used in the place of the combustion device. The term "catalytic combustion device" as used herein means a device which is packed with a heretofore well-known catalyst having a noble metal deposited or not deposited thereon. The acrylic acid waste gas or ester waste gas which has been heated to an elevated temperature, for example, is introduced into the catalytic combustion device so as to have the organic component contained in the waste gas oxidized by combustion. Even when the catalytic combustion device is used, it is still preferable to have the ester acid waste gas diluted with the acrylic acid waste gas as described above because the operation of this device entails such problems as suffering the catalyst to be deteriorated by the ester acid waste gas.

The method of this invention for treating the waste material is effected in one preferred embodiment thereof by using the acrylic acid waste oil and the ester waste oil as fuels for combustion and adding to the acrylic acid waste water or the ester waste water for the sake of adjusting the viscosity of the acrylic acid waste oil. It is nevertheless preferable to perform the treatment for wet oxidation on the ester waste water which is not subjected to the treatment for combustion. This is because the ester waste water exhibits a low COD level and suits the treatment for wet oxidation, because the treatment for wet oxidation requires no fuel for combustion, and further because the waste water resulting from the treatment has such high purity as renders the ester waste water reusable. Though the treatment with activated sludge can be adopted in this case as a matter of course, it consumes much time in decomposing the organic substance and encounters difficulty in performing the treatment quickly. Further, the waste water is required to be diluted to a concentration suitable for the growth of algae and bacteria and the activated sludge facility is required to have a wide area. Thus, the use of the heretofore well-known device for the treatment of wet oxidation render the treatment simple and convenient to perform.

This invention permits the treated water which has undergone the purification mentioned above to be used again in the process for production of acrylic acid and/or the process for production of acrylic ester mentioned above. In the process for production of acrylic acid, a large amount of water is used as the absorbent during the absorption of acrylic acid. This water is discharged from the azeotropic dehydrating column. Part of the water is circulated as the absorbent to the absorption column and reused therein and part there of is disposed of as a waste water. In this invention, the treated water which has been purified by the treatment of wet oxidation can be used as the absorbent for acrylic acid.

EXAMPLES

Now, this invention will be specifically described below with reference to working examples.

Example 1

Acrylic acid and an acrylic ester were produced by following the procedure depicted in FIG. 1. First, a raw material gas containing propylene was subjected to gas phase oxidation to form an acrylic acid-containing gas. The gas was supplied to an absorption column and treated therein with water as an absorbent to absorb acrylic acid and consequent formation of an acrylic acid-containing solution. Then, the solution was supplied to an azeotropic dehydrating column and distilled therein in the presence of an azeotropic solvent to separate low boiling impurity through the top of the column. After the oil-aqueous separation, the aqueous phase 32 was obtained as waste water at a rate of 2.0 $m^3/h$. The bottom liquid of the azeotropic dehydrating column was supplied to a heavy-ends cut column and distilled therein to separate acrylic acid through the top of the column. When the bottom liquid 43 of the heavy-ends cut column was further concentrated with a thin film evaporator, a waste oil was obtained at a rate of 440 kg/h.

Part of the acrylic acid obtained from the heavy-ends cut column was esterified with ethyl alcohol, n-butyl alcohol, and 2-ethylhexyl alcohol to produce ethyl acrylate, n-butyl acrylate, and 2-ethylhexyl acrylate. In the process for production of the acrylic ester, waste water was obtained at a total rate of 3.7 $m^3/h$ from the waste water 61 of the distilling column and the water phase 72 of the oil-aqueous separating device and waste oil was obtained at a rate of 555 kg/h from the bottom of the heavy-ends cut column 110.

The whole amount of the waste oil obtained from the acrylic acid and acrylic esters mentioned above and part (the portion balanced with the combustion of the waste oil) of the waste water from the process for production of acrylic acid and the process for production of acrylic esters were supplied to a vertical waste liquid combustion device and burnt therein at 950° C.

When the interior of the furnace was inspected after one month's operation of the device, it showed practically no sign of a deposit thereon. The waste water was stripped in the stripping column by the use of the exhaust gas from the combustion device. The gas emanating through the top of the column was supplied directly to the combustion device and the concentrated bottom liquid of the column was supplied directly to the combustion device.

The residual waste water obtained from the process for production of an acrylic ester mentioned above was supplied to the device for treatment of wet oxidation and treated therein at 260° C. The treated water was recovered at a rate of 0.5 $m^3/h$ as an absorbent for use in the device handling acrylic acid.

Example 2

An acrylic acid-containing gas was obtained by subjecting a raw material gas containing propylene to gas phase oxidation by following the procedure illustrated in FIG. 1 with necessary modifications. The gas was supplied to an absorption column and treated therein by the use of an absorbent to obtain an acrylic acid-containing solution. The absorption column emitted a gas containing 900 vol. ppm of acrylic acid and 20.8 vol. % of water at a rate of 610 $Nm^3$/min.

Then, similarly to the procedure of Example 1, the solution was supplied to the azeotropic dehydrating column and distilled therein in the presence of an azeotropic solvent to separate low boiling impurity via the top of the column. The bottom liquid of the azeotropic dehydrating column was supplied to a heavy-ends cut column and distilled therein to separate acrylic acid through the top of the column. The bottom liquid of the heavy-ends cut column was further concentrated in a thin film evaporator.

Part of the acrylic acid obtained from the heavy-ends cut column was esterified with ethyl alcohol, n-butyl alcohol, and 2-ethylhexyl alcohol to produce ethyl acrylate, n-butyl acrylate, and 2-ethylhexyl acrylate.

The waste gas emanating from the tank of acrylic acid and the tank of an acrylic ester was diluted with air supplied by a blower to obtain waste gas at a rate of 30 $Nm^3$/min.

The waste gas mentioned above was supplied to the same device for catalytic combustion as mentioned above, heated to an elevated temperature with a plate heat exchanger, and then burnt in the device for catalytic combustion.

When the interior of the furnace was inspected after one month's operation of the device, it showed practically no sign of a deposit thereon. The treated gas was used as a gas for sealing the tank of an acrylic ester.

Example 3

By following the procedure illustrated in FIG. 1 with necessary modifications, a raw material gas containing propylene was subjected to gas phase oxidation to produce an acrylic acid-containing gas. The gas was supplied to an absorption column and treated therein in the presence of an absorbent to obtain an acrylic acid-containing solution. The absorption column emitted a gas containing 900 vol. ppm of acrylic acid and 20.8 vol. % of water at a rate of 610 $Nm^3$/min through the top thereof.

Then, by following the procedure of Example 1, the solution was supplied to an azeotropic dehydrating column and distilled therein in the presence of an azeotropic solvent to separate a water-containing low boiling impurity through the top of the column. After the oil-aqueous separation, the aqueous phase was obtained as waste water at a rate of 1.7 $m^3$/h. The bottom liquid of the azeotropic dehydrating column was supplied to a heavy-ends cut column and distilled therein to separate acrylic acid through the top thereof.

Part of the acrylic acid obtained from the heavy-ends cut column was esterified with ethyl alcohol, n-butyl alcohol, and 2-ethylhexyl alcohol to produce ethyl acrylate, n-butyl acrylate, and 2-ethylhexyl acrylate.

The waste gas emanating from the tank for acrylic acid and the tank for an acrylic ester was diluted with air supplied by the use of a blower to obtain waste gas at a rate of 30 $Nm^3$/min.

The waste gas and the waste water mentioned above were supplied to the same combustion device as mentioned above and burnt therein with natural gas as the fuel till the temperature of the interior of the furnace reached 900° C. An innoxious gas produced in the furnace was released into the ambient air.

The invention claimed is:

1. A method for the disposal of waste material, which comprises the steps of combusting a mixed liquid comprising at least one waste material selected from the group consisting of waste oil and waste water emitted from a process for production of acrylic acid and at least one waste material selected from the group consisting of waste oil and waste water emitted from a process for production of an acrylic ester jointly.

2. A method according to claim 1, wherein part of the waste water is treated for combustion and the remainder thereof is subjected to wet oxidation and/or treatment with activated sludge.

3. A method according to claim 1, which further comprises obtaining a treated water and/or a treated gas by the purification, and reusing the treated water and/or the treated gas for said process for production of acrylic acid and/or said process for production of an acrylic ester.

4. A method for the disposal of waste material emitted from a process for production of polyacrylic acid and/or the salt thereof, which comprises the steps of mixing at least one waste material selected from the group consisting of waste oil, waste water, and waste gas emitted from a process for production of acrylic acid and at least one waste material selected from the group consisting of waste oil, waste water, and waste gas emitted from a process for production of an acrylic ester jointly, and combusting the mixture thus formed.

5. A method according to claim 4, wherein part of the waste water is treated for combustion and the remainder thereof is subjected to wet oxidation and/or a treatment with activated sludge.

6. A method according to claim 4, which further comprises the steps of obtaining a treated water and/or a treated gas by the purification, and reusing the treated water and/or the treated gas for said process for production of acrylic acid and/or said process for production of an acrylic ester.

7. A method according to claim 4, wherein the acrylic acid waste water or the acrylic ester waste water is added to the acrylic acid waste oil in an amount of 3–30% vol. based on the volume of the acrylic acid waste oil.

8. A method according to claim 4, wherein the acrylic acid waste water and the acrylic ester waste water is added to the acrylic acid waste oil in an amount of 3–30% vol. based on the volume of acrylic acid waste oil.

9. The method of claim 1 wherein the mixed liquid is said waste oil from a process for production of acrylic acid and said waste water from a process for production of acrylic acid.

* * * * *